United States Patent
Hsiung et al.

(10) Patent No.: US 7,883,668 B2
(45) Date of Patent: Feb. 8, 2011

(54) OPTICAL BLOOD GAS SENSOR FOR REAL TIME MEASUREMENT

(75) Inventors: Shen-Kan Hsiung, Tao-Yuan (TW); Jung-Chuan Chou, Tao-Yuan (TW); Tai-Ping Sun, Tao-Yuan (TW); Nien-Hsuan Chou, Tao-Yuan (TW); Chih-Wei Lai, Tao-Yuan (TW)

(73) Assignee: Chung Yuan Christian University, Tao-Yuan (TW)

( * ) Notice: Subject to any disclaimer, the term of this patent is extended or adjusted under 35 U.S.C. 154(b) by 542 days.

(21) Appl. No.: 11/949,563

(22) Filed: Dec. 3, 2007

(65) Prior Publication Data

US 2008/0194040 A1    Aug. 14, 2008

(30) Foreign Application Priority Data

Dec. 28, 2006    (TW) .............................. 95149390 A (51) Int. Cl.
*G01J 1/48* (2006.01)
(52) U.S. Cl. .............................. 422/86; 422/55; 422/58; 422/83; 422/82.04
(58) Field of Classification Search .................... 422/55, 422/58, 83, 86, 82.04
See application file for complete search history.

(56) References Cited

U.S. PATENT DOCUMENTS

| | | | | |
|---|---|---|---|---|
| 5,403,746 A | * | 4/1995 | Bentsen et al. | ................ 436/68 |
| 7,740,904 B2 | * | 6/2010 | Shahriari | .................... 427/157 |

* cited by examiner

*Primary Examiner*—Jill Warden
*Assistant Examiner*—M. Cole
(74) *Attorney, Agent, or Firm*—WPAT, PC; Justin King (57) ABSTRACT

An optical gas concentration sensor and method for measuring blood gas based on the light adsorption sensing technique are disclosed. The optical gas concentration sensor comprises a light source, a photo detector, and a gas filtering membrane for separating the indicator and a liquid. A gas in the liquid diffuses to the indicator through the gas filtering membrane so as to change the color of the indicator due to the chemical reaction occurred between the indicator and the gas. Then, the photo detector receives the light passing though the reacted indicator from the light source. The gas concentration is determined based on pH-sensitive absorbance spectrum of the indicator.

12 Claims, 7 Drawing Sheets

OPTICAL BLOOD GAS SENSOR FOR REAL TIME MEASUREMENT

BACKGROUND OF THE INVENTION

1. Field of the Invention

The present invention generally relates to sensors, especially an optical gas concentration sensor.

2. Description of the Prior Art

Blood analyzers help patients manage their own health conditions in a more cost-effective and convenient way before seeking a doctor for further diagnosis and treatment. Not only can patients monitor their health conditions by checking the densities of eight major parameters whenever they wish, but the information can also be provided to the doctors to facilitate diagnosis. When measuring the concentration of carbon dioxide, sensors that can provide stable and continuous measurements are needed.

Conventional electrodes for sensing the concentration of carbon dioxide, for example a biomedical sensing system called i-STAT® available from Abbott Laboratories, U.S.A., are very accurate but expensive. Moreover, there are problems such as gas content in blood may be consumed during measurement and their size being large, making them unsuitable for continuous intrusion-type measurements. Since the size of the overall sensing system is usually bulky, they are not suitable for home care use, and may cause discomfort to users. Mobility and accuracy in measurement are also affected. Therefore, there is a need for an improved design that simplifies its structure and enhances its operating comfort.

SUMMARY OF THE INVENTION

In view of the prior art and the needs of the related industries, the present invention provides an optical gas concentration sensor that solves the abovementioned shortcomings of the conventional gas concentration sensors.

One objective of the present invention is to provide a gas concentration sensor having a separating structure that utilizes the facts that an indicator may change its color when reacting with a gas contained in a liquid and that the changed color of the indicator may alter its light adsorption characteristic, thus allowing stable sensing and continuous measurement easy to implement. Another objective of the present invention is to employ a light source for emitting light and a photo detector for receiving light passing through reacted indicator and outputting a sensing signal corresponding to the intensity of received light, so as to detect pH variation in the liquid, thus providing an easy and non-intrusive measuring method.

According to the above and other objectives, the present invention discloses an optical gas concentration sensor based on the light adsorption sensing technique. The optical gas concentration sensor comprises a gas filtering membrane for separating the indicator and a liquid. A gas in the liquid diffuses to the indicator through the gas filtering membrane to change the color of the indicator due to the chemical reaction occurred between the indicator and the diffused gas. Then, a light source is used to irradiate light on the reacted indicator and a photo detector is used to receive the light passing though the reacted indicator and output a sensing signal corresponding to the intensity of received light, so as to detect pH variation in the liquid.

BRIEF DESCRIPTION OF THE DRAWINGS

The accompanying drawings incorporated in and forming a part of the specification illustrate several aspects of the present invention, and together with the description serve to explain the principles of the disclosure. In the drawings.

DETAILED DESCRIPTION OF THE PREFERRED EMBODIMENTS

The present invention is directed to an optical gas concentration sensor. Detailed steps and constituents are given below to assist in the understanding the present invention. Obviously, the implementations of the present invention are not limited to the specific details known by those skilled in the art. On the other hand, well-known steps or constituents of digital watermarking are not described in details in order not to unnecessarily limit the present invention. Detailed embodiments of the present invention will be provided as follow. However, apart from these detailed descriptions, the present invention may be generally applied to other embodiments, and the scope of the present invention is thus limited only by the appended claims.

A first embodiment of the present invention discloses an optical gas concentration sensor, including a gas filtering device, an indicator, a light source and a photo detector. A gas contained in a liquid inside a container diffuses into the gas filtering device in which the indicator resides. The indicator then reacts with the gas diffused into the gas filtering device, and changes its color as a result of the reaction. The light source provided on one side of the gas filtering device is used to emit light through the reacted indicator. The photo detector is located on the other side of the gas filtering device, wherein the light source and the photo detector are on opposite sides of the gas filtering device. The photo detector receives the light that passes through the reacted indicator, and outputs a sensing signal according to the intensity of the received light, thereby determining pH variation of the liquid.

In this embodiment, the gas filtering device may include a light filter. The light filter has an opening disposed between the light source and the photo detector, in which the optical path between the light source and the photo detector penetrates the opening of the light filter. The gas filtering device is a transmissive material, which may be silica gel for example. The gas filtering device may further include a gas filtering membrane. The gas in the liquid diffuses into the gas filtering device via the gas filtering membrane. The light source may include one selected from laser light source and light-emitting diode light source. The wavelength of the light source is approximately 525 nm. The light source is only exemplary, and may be replaced by other light sources known to those skilled in the art. The photo detector may be detector that converts light to electricity or other kind of photo detector, and the present invention is not limited to these. Furthermore, the indicator is a pH indicator, its acidity response is buffered by a bicarbonate solution and may include one selected from the following: general indicator, phenol red, bromthymol blue or other indicators known to those skilled in the art.

Figure 1A:
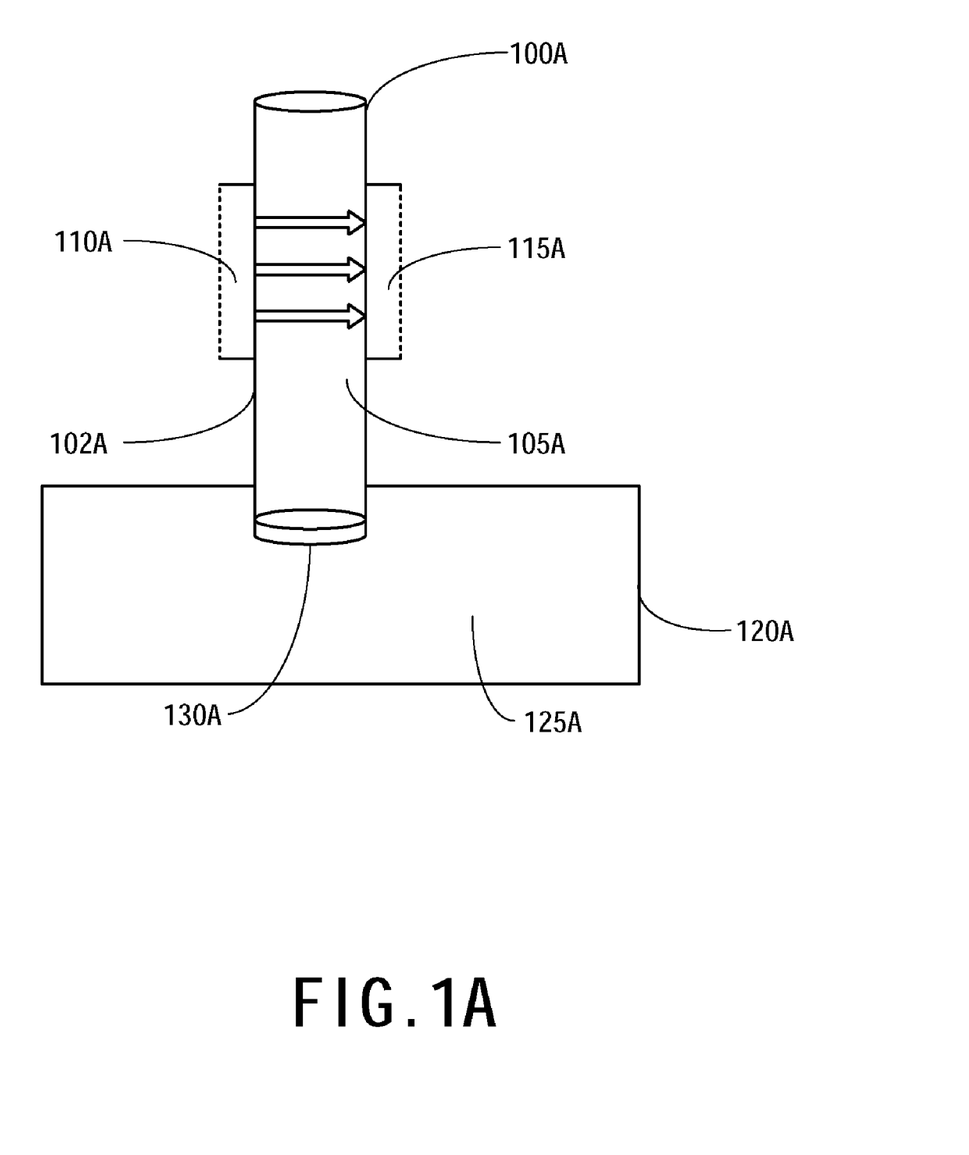
FIG. 1A is a schematic diagram of an optical gas concentration sensor in a first embodiment of the present invention.

As shown in FIG. 1A, in a preferred embodiment of the present invention, an optical gas concentration sensor 100A includes a gas filtering device 102A, an indicator 105A, a laser light source 110A and a photo detector 115A. A gas contained in a liquid 125A inside a container 120A diffuses into the gas filtering device 102A. The laser light source 110A is provided on one side of the gas filtering device 102A, while the photo detector 115A is located on the other side of the gas filtering device 102A, wherein the laser light source 110A and the photo detector 115A are on opposite sides of the gas filtering device 102A. The gas filtering device 102A further includes a gas filtering membrane 130A, via which the gas contained in the liquid 125A diffuses into the gas filtering device 102A.

Figure 1B:
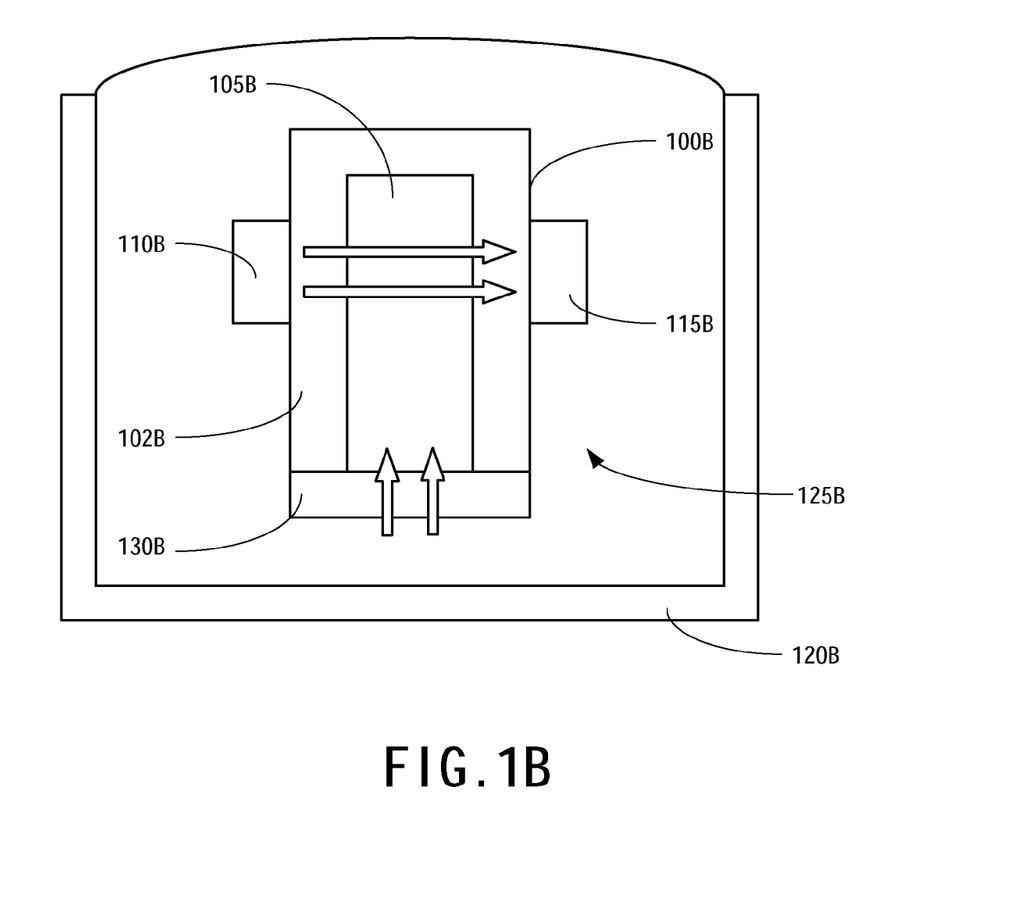
FIG. 1B is a schematic diagram of a disposable optical gas concentration sensor in the first embodiment of the present invention.

As shown in FIG. 1B, in a preferred embodiment of the present invention, a disposable optical gas concentration sensor 100B includes a gas filtering device 102B, an indicator 105B, a light-emitting diode light source 110B, and a photo detector 115B. A gas contained in a liquid 125B inside a container 120B diffuses into the gas filtering device 102B. The light-emitting diode light source 110B is provided on one side of the gas filtering device 102B, while the photo detector 115B is located on the other side of the gas filtering device 102B, wherein the light-emitting diode light source 110B and the photo detector 115B are on opposite sides of the gas filtering device 102B. The gas filtering device 102B further includes a gas filtering membrane 130B, via which the gas contained in the liquid 125B diffuses into the gas filtering device 102B.

Figure 1C:
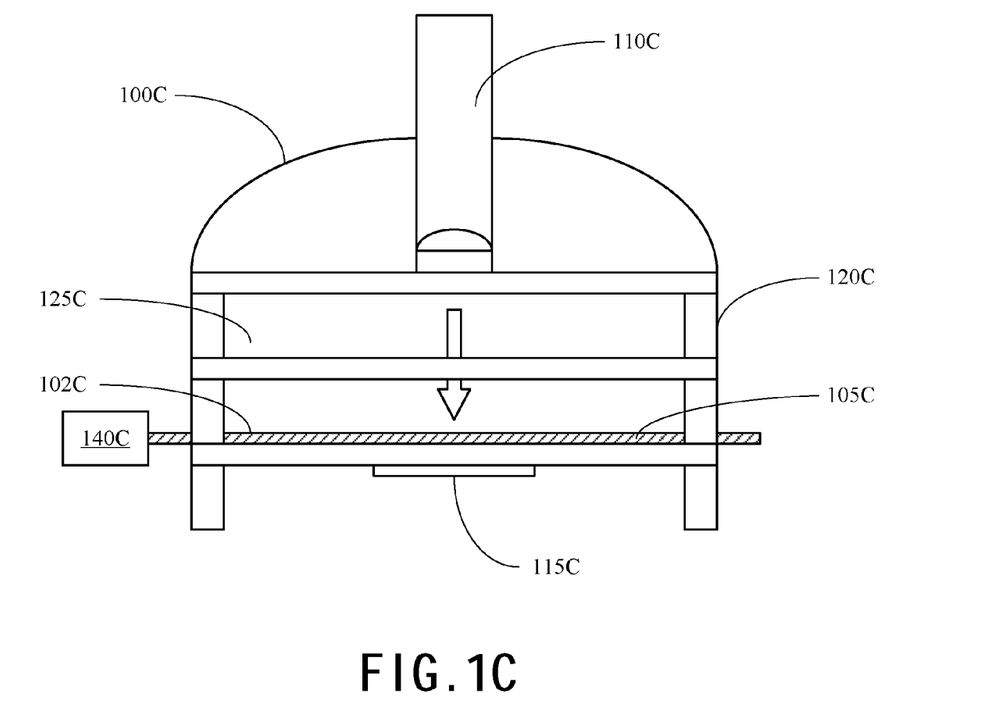
FIG. 1C a schematic diagram of a portable optical gas concentration sensor in the first embodiment of the present invention.

As shown in FIG. 1C, in a preferred embodiment of the present invention, a portable optical gas concentration sensor 100C includes a gas filtering device 102C, an indicator 105C, a light source 110C, a photo detector 115C and a dynamic flow device 140C. A gas contained in a liquid 125C inside a container 120C diffuses into the gas filtering device 102C. The light source 110C is provided on one side of the gas filtering device 102C, while the photo detector 115C is located on the other side of the gas filtering device 102C, wherein the light source 110C and the photo detector 115C are on opposite sides of the gas filtering device 102C. The dynamic flow device 140C is used to replace the indicator 105C, in the optical path between the light source 110C and the photo detector 115C, that has already reacted with the gas with the indicator 105C that has not yet reacted with the gas.

Figure 2A:
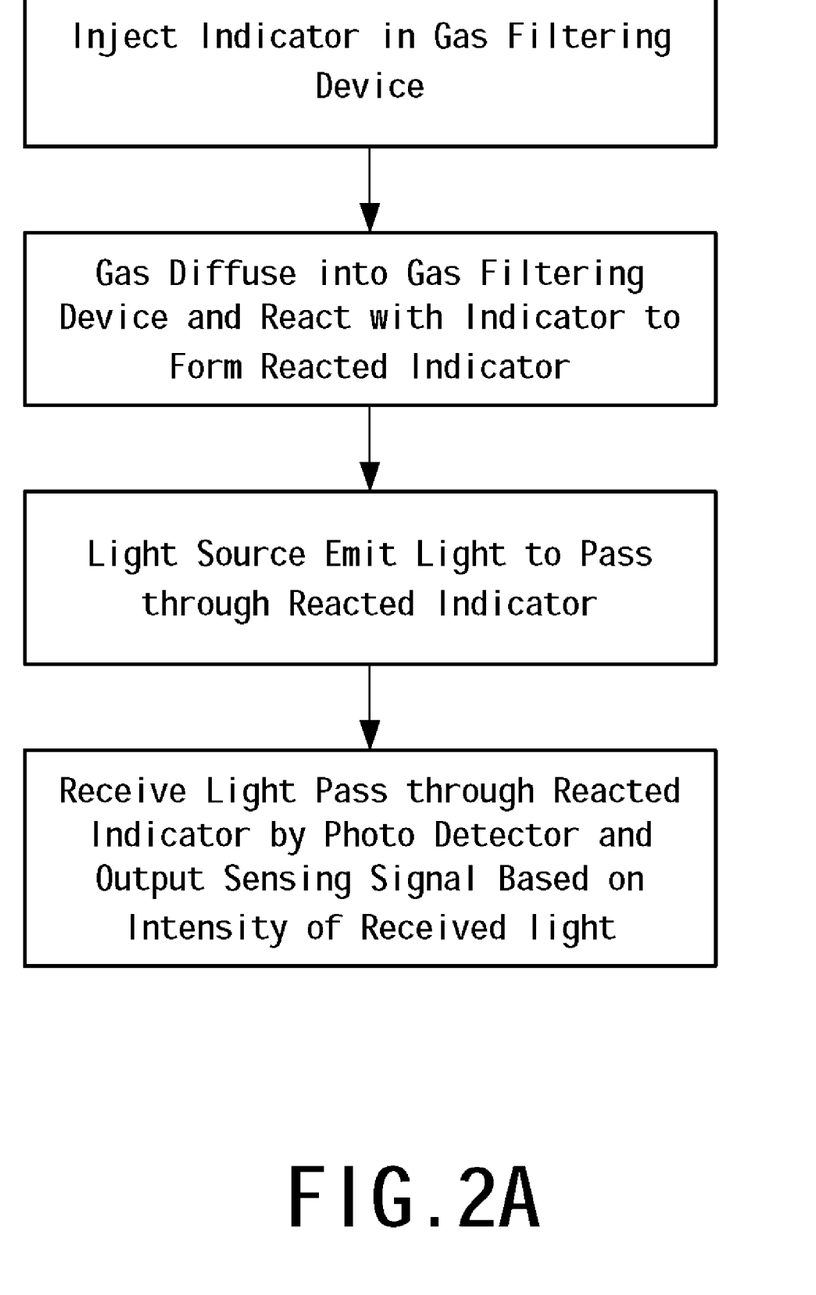
FIG. 2A is a flow chart illustrating a preferred embodiment of a method for optically sensing gas concentration in a second embodiment of the present invention.

A second embodiment of the present invention discloses a method for optically sensing gas concentration. As shown in FIG. 2A, first, a portion of a gas filtering device is placed in the liquid in a container, wherein the gas filtering device includes a gas filtering membrane and an indicator, such that a gas in the liquid diffuses into the gas filtering device through the gas filtering membrane and contacts the indicator. Then, a light source is irradiated on the gas filtering device. A photo detector then receives the light transmitted through the gas filtering device emitted by the light source. Thereafter, the concentration of the gas is determined based on the intensity of the light received by the photo detector.

Figure 2B:
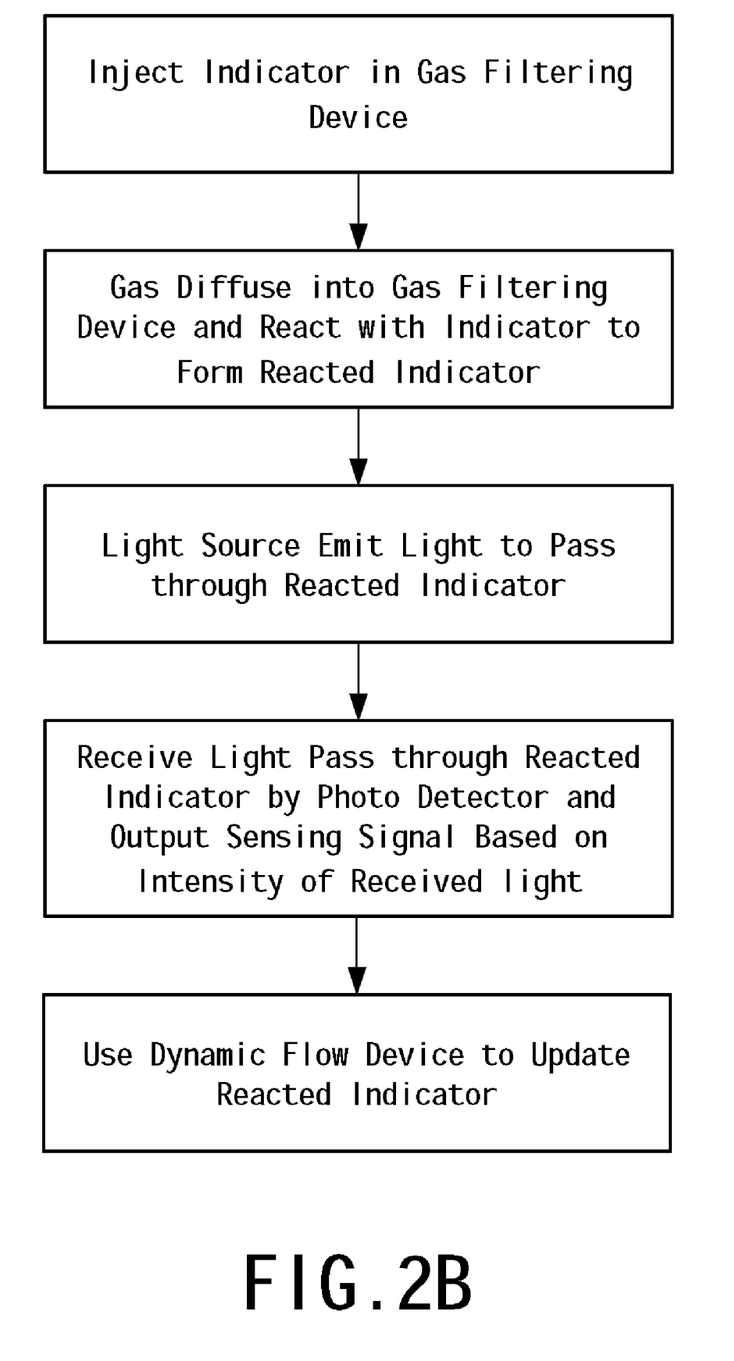
FIG. 2B is a flow chart illustrating another preferred embodiment of a method for optically sensing gas concentration in the second embodiment of the present invention.

In a preferred embodiment of the present invention, as shown in FIG. 2B, the method for optically sensing gas concentration further includes a step of using a dynamic flow device to replace the indicator already reacted with the gas in the optical path between the light source and the photo detector with the indicator not yet reacted with the gas. The gas filtering device may include a light filter that has an opening disposed between the light source and the photo detector. The optical path between the light source and the photo detector passes through the opening of the light filter. The gas filtering device is a transmissive material, which may be silica gel for example. The gas filtering device may further include a gas filtering membrane. The gas in the liquid diffuses into the gas filtering device via the gas filtering membrane. The light source may include one selected from laser light source and light-emitting diode light source. The wavelength of the light source is approximately 525 nm. The light source is only exemplary, and may be replaced by other light sources known to those skilled in the art. The photo detector may be detector that converts light to electricity or other kind of photo detector, and the present invention is not limited to these. Furthermore, the indicator is a pH indicator, its acidity response is buffered by a bicarbonate solution and may include one selected from the following: general indicator, phenol red, bromthymol blue or other indicators known to those skilled in the art.

Figure 3:
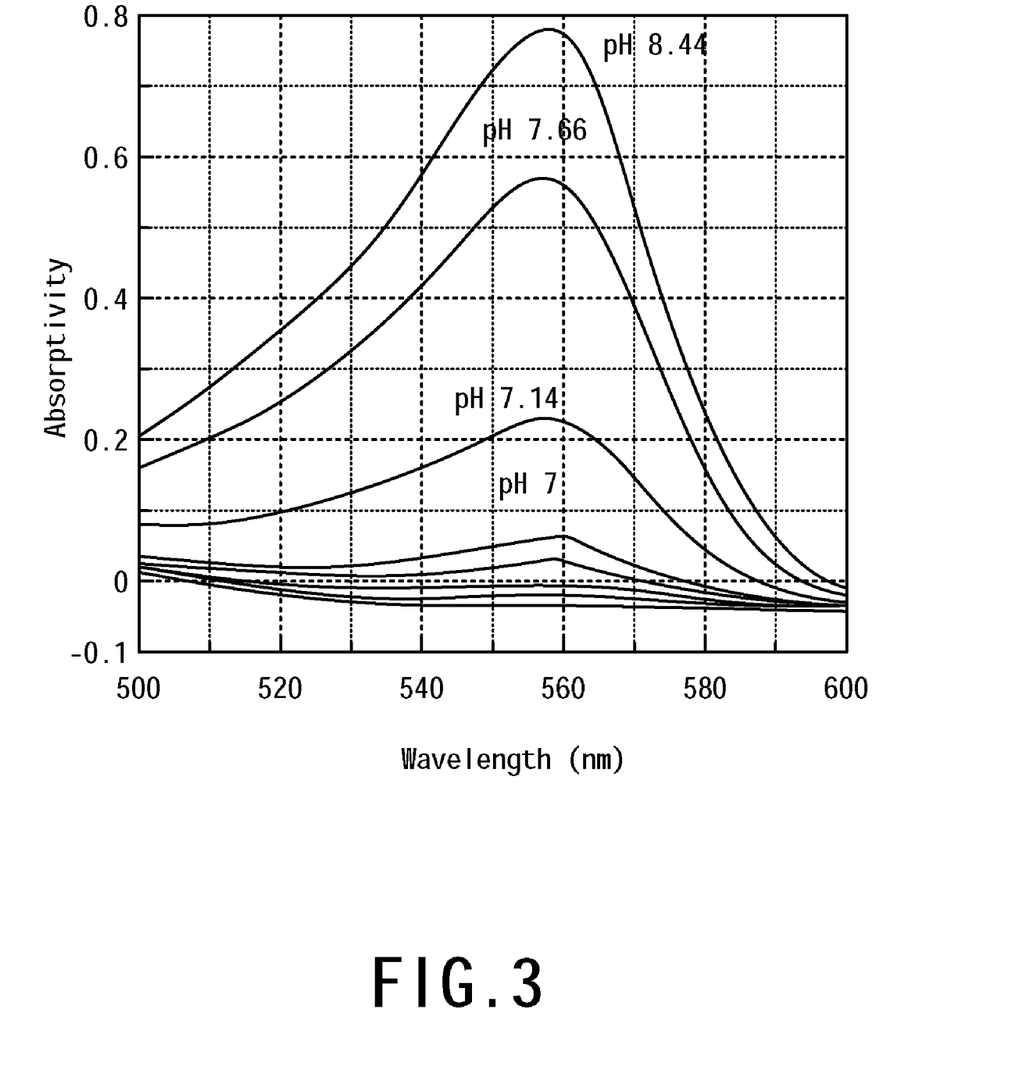
FIG. 3 is a graph showing relationship between liquid pH values versus an absorption characteristic of a spectrum of an indicator in the first embodiment of the present invention.

One preferred embodiment of the present invention uses an optical-absorption-based optical gas concentration sensor, wherein the optical absorptivity of the indicator varies with the amount of diffused gas. Since the indicating range of phenol red is between pH 6.8 and pH 8.4, so in order to test the concentration within the normal range of the human body, a bicarbonate solution is added and the concentration of the buffer is controlled to increase the resolution. As shown in FIG. 3, the absorption characteristic of the spectrum of phenol red indicator is that the optical absorption decreases along with the increase of pH value. The optimum sensing wavelength is approximately 555 nm. It is obvious that no absorption characteristic is found in the band of red light.

Figure 4:
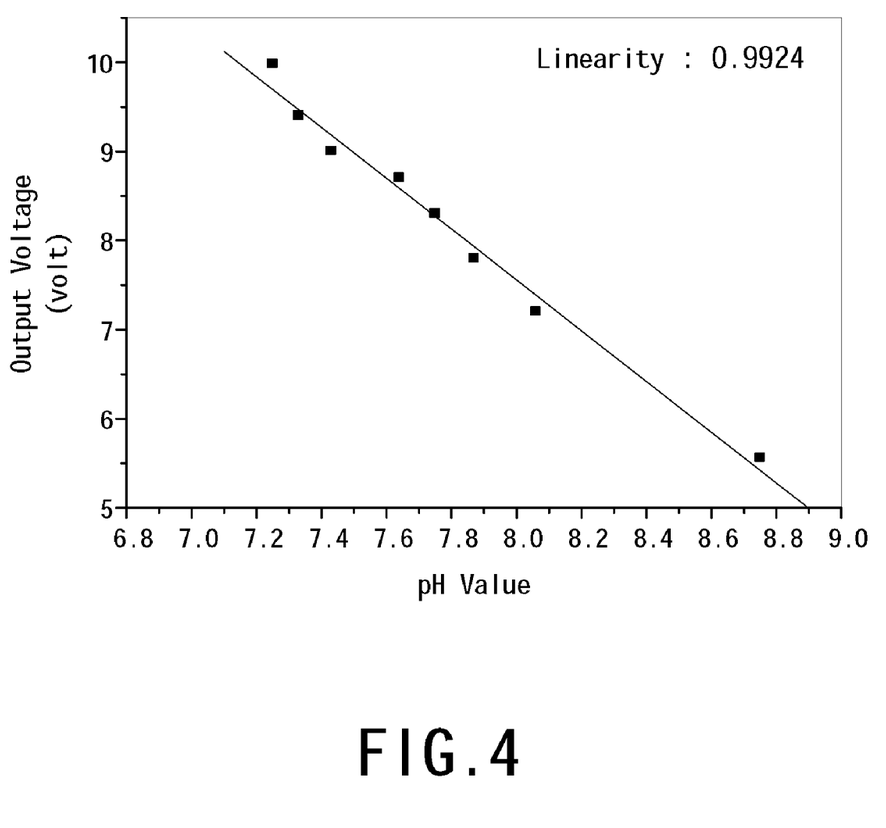
FIG. 4 is a graph showing the relationship between responses for a sensor measuring in the range between pH 6.8 to pH 8.4 and output voltage variation of a photo detector in the first embodiment of the present invention.

Another preferred embodiment of the present invention includes raising the signal-to-noise ratio (SNR) of the output end versus the original sensing signal by employing a laser light source with optical characteristics such as high focus, power and accuracy. This makes it suitable for extraction of minute electrical signal in biological sensors. Then, a surface mounted (SMD) photo detector is used to extract the minute electrical signal in the sensor, thus maintaining high SNR and improving the quality of the output signal. The, a membrane switch reduces disturbance to the minute electrical signal in the sensor caused by vibrations to facilitate subsequent processing. Thereafter, the optical path is adjusted to increase the resolution of the sensor, so that the output signal complies with output limits and standards for clinical laboratories. As shown in FIG. 4, the sensor measures response in the range between pH 6.8 and pH 8.4 and the output voltage of the sensor has an inverse linear relationship with the pH values.

The foregoing description is not intended to be exhaustive or to limit the invention to the precise forms disclosed. Obvious modifications or variations are possible in light of the above teachings. In this regard, the embodiment or embodiments discussed were chosen and described to provide the best illustration of the principles of the invention and its practical application to thereby enable one of ordinary skill in the art to utilize the invention in various embodiments and with various modifications as are suited to the particular use contemplated. All such modifications and variations are within the scope of the inventions as determined by the appended claims when interpreted in accordance with the breath to which they are fairly and legally entitled.

It is understood that several modifications, changes, and substitutions are intended in the foregoing disclosure and in some instances some features of the invention will be employed without a corresponding use of other features. Accordingly, it is appropriate that the appended claims be construed broadly and in a manner consistent with the scope of the invention.

The invention claimed is:

1. An optical gas concentration sensor including:
   a gas filtering device, wherein a gas contained in a liquid in a container diffuses into the gas filtering device;
   an indicator in the gas filtering device, wherein the indicator reacts with the gas diffused into the gas filtering device;
   a light source provided on a side of the gas filtering device;
   a photo detector provided on another side of the gas filtering device, wherein the light source and the photo detector are on the opposite sides of the gas filtering device; and
   a dynamic flow device used for replacing the indicator already reacted with the gas in an optical path between the light source and the photo detector with the indicator not yet reacted with the gas.

2. An optical gas concentration sensor of claim 1, wherein the gas filtering device further includes a light filter that comprises an opening between the light source and the photo detector, wherein an optical path between the light source and the photo detector passes through the opening.

3. An optical gas concentration sensor of claim 1, wherein the gas filtering device includes a transmissive material.

4. An optical gas concentration sensor of claim 1, wherein the material of the gas filtering device is silica gel.

5. An optical gas concentration sensor of claim 1, wherein the gas filtering device includes a gas filtering membrane, via which the gas in the liquid diffuses into the gas filtering device.

6. An optical gas concentration sensor of claim 5, wherein the gas filtering membrane is dipped in the liquid.

7. An optical gas concentration sensor of claim 1, wherein the light source is one selected from the group consisting of a laser light source and a light-emitting diode light source.

8. An optical gas concentration sensor of claim 1, wherein the wavelength of the light source is approximately 525 nm.

9. An optical gas concentration sensor of claim 1, wherein the photo detector is a photo detector that converts light to electricity.

10. An optical gas concentration sensor of claim 1, wherein an acidity response of the indicator is buffered by a bicarbonate solution.

11. An optical gas concentration sensor of claim 1, wherein the indicator is a pH indicator.

12. An optical gas concentration sensor of claim 1, wherein the indicator comprises phenol red or bromthymol blue.

* * * * *